US00PP11318P

United States Patent [19]

Heims

[11] Patent Number: Plant 11,318

[45] Date of Patent: Mar. 28, 2000

[54] ***MYOSOTIS SYLVATICA* PLANT NAMED 'GOLD 'N SAPPHIRES'**

[75] Inventor: Dan M. Heims, Portland, Oreg.

[73] Assignee: Terra Nova Nurseries, Inc., Portland, Oreg.

[21] Appl. No.: 09/060,155

[22] Filed: Apr. 14, 1998

[51] Int. Cl.[7] ..... A01H 5/00

[52] U.S. Cl. ..... Plt./263

[58] Field of Search ..... Plt./263

*Primary Examiner*—Howard J. Locker
*Assistant Examiner*—Wendy A Baker
*Attorney, Agent, or Firm*—Klarquist Sparkman Campbell Leigh & Whinston, LLP

[57] ABSTRACT

A new and distinct form of Myosotis characterized by unusual golden foliage and compact habit.

1 Drawing Sheet

The present invention relates to a new and distinct seedling of *Myosotis sylvatica* (normally with green foliage) showing unusual golden coloration of the leaves.

The new Myosotis is a result of an open-pollinated seedling selection of an unnamed and unpatented variety of *Myosotis sylvatica* in the family Boraginaceae (Borage family) at Terra Nova Nurseries, Inc., in Canby, Oreg. This was selected from a large group of seedlings. Type plants of *Myosotis sylvatica* were retained to observe habit and to compare with the new variety. The new variety has been reproduced only by asexual propagation (division and tissue culture). Each of the progeny exhibits identical characteristics to the original plant and is unlike any Myosotis offered by any American nursery or book (known to me) as evidenced by the following characteristics:

(1) Summer, fall and winter: Golden foliage with occasional green mottling.

(2) Spring: Very gold foliage with occasional green mottling, very tight cobalt to violet-blue flowers.

Asexual propagation by division and tissue-culture as done in Tigard, Oreg., shows that the foregoing characteristics and distinctions come true to form and are established and transmitted through succeeding propagations.

BRIEF DESCRIPTION OF THE PHOTOGRAPH

The FIGURE shows a two-year-old clump of *Myosotis sylvatica* 'Gold 'n Sapphires' blooming in April.

DETAILED PLANT DESCRIPTION

The following is a detailed description of the new Myosotis hybrid based on observations of specimens in Canby, Oreg. The color descriptions are all based on The *Royal Horticultural Society Colour Chart* and the *American Rhododendron Society* publication: "A CONTRIBUTION TOWARD STANDARDIZATION OF COLOR NAMES IN HORTICULTURE."

Foliage:

*Type.*—Simple; herbaceous.
*Shape.*—Linear-spatulate.
*Length.*—7 cm.–8 cm.
*Width.*—2.25 cm.
*Petiole length.*—4–6.5 cm.
*Margins.*—Entire, ciliate.
*Apex.*—Obtuse.

*Base.*—Cuneate.
*Leaf texture.*—Sericeous (silky).
*Petiole texture.*—Finely pilose.
*Leaf arrangement.*—Tightly alternate.
*Venation.*—Camptodrome.

Size:

*Height.*—18 cm (2-yr-old plant in Oregon grown from a 3-cm plug).
*Width.*—27 cm (2-yr-old plant in Oregon grown from a 3-cm plug).

Flower:

*Petal count.*—5.
*Petal shape.*—Spatulate-truncate, slightly recurved.
*Flower type.*—Complete; calyx tube lobed, urn-shaped.
*Flower size.*—8 mm.
*Flower number.*—5 to 15 per cyme.
*Blooming habit.*—Dense cymes over a mound-shaped plant.
*Bloom period.*—March 15 to May 15 (in Western Oregon).

Color characteristics:

Foliage:

*Mature leaves upper surface —spring/early summer.*—R.H.S. 151 C Yellow Green group (Strong Greenish Yellow ARS) with occasional mottling R.H.S. 137 A to 138 A Green group.
*Upper surface, late summer through winter.*—R.H.S. 144 B Yellow Green group (Strong Yellow Green ARS) with occasional mottling R.H.S. 137 A to 138 A Green group.
*Lower surface.*—R.H.S. 147C Yellow Green group (Moderate Yellow Green ARS).

Flowers: R.H.S. 98B Violet Blue group (Strong Purplish Blue ARS) fading to R.H.S. 75B Purple group.

DESCRIPTION OF THE ORIGINAL PLANT

The seed parent is identical to the new variety in every way except for leaf coloration. The seed parent has uniformly green leaves whereas the new variety is characterized by unusual golden foliage.

I claim:

1. A new and distinct hybrid of Myosotis plant substantially as shown and described, characterized by unusual golden foliage and compact habit.

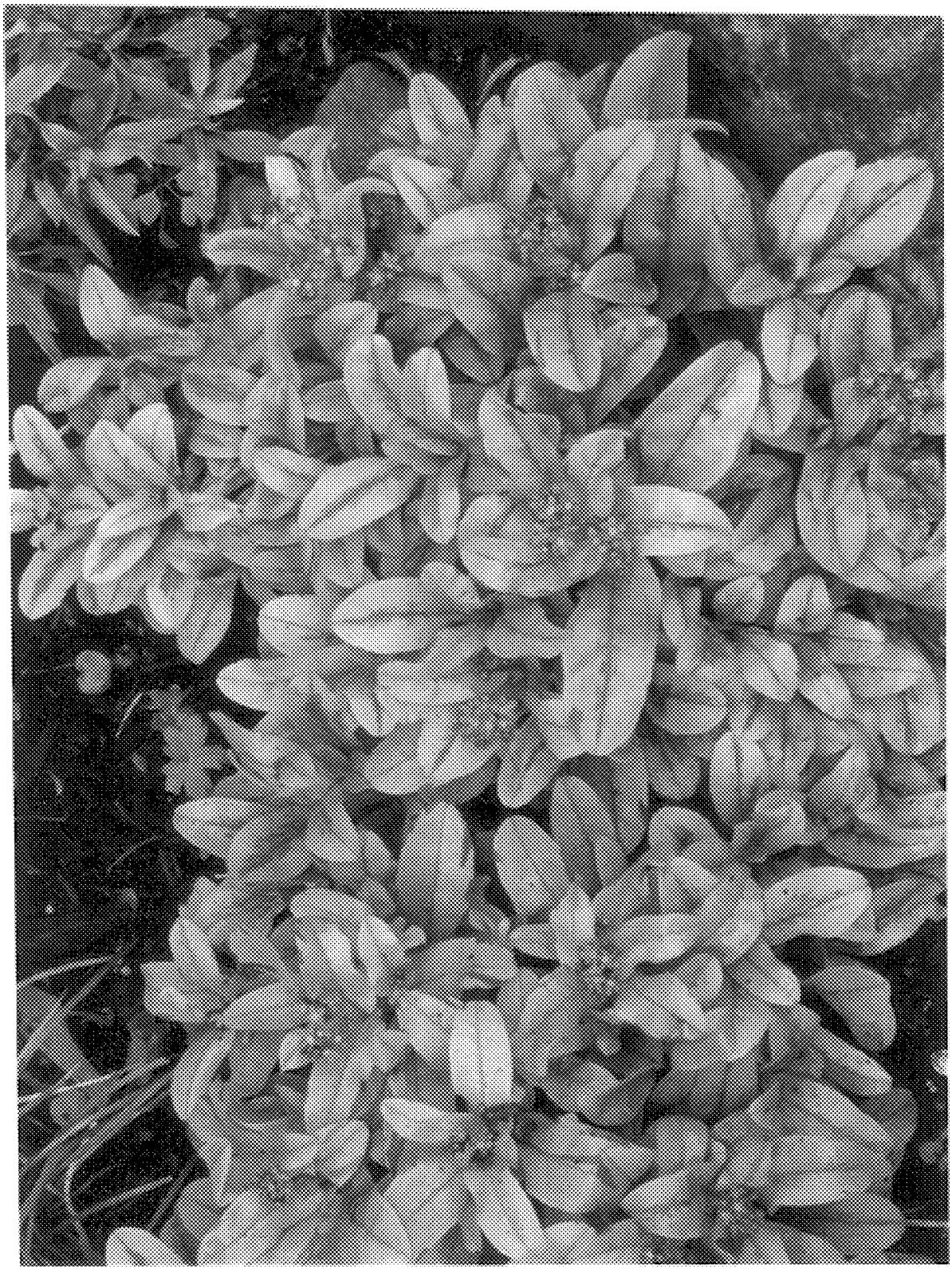

* * * * *